United States Patent
Belgorodsky et al.

(10) Patent No.: US 9,591,853 B2
(45) Date of Patent: Mar. 14, 2017

(54) JELLYFISH-DERIVED POLYMER

(71) Applicant: RAMOT AT TEL-AVIV UNIVERSITY LTD., Tel Aviv (IL)

(72) Inventors: Bogdan Belgorodsky, Tel Aviv, IL (US); Ludmila Fadeev, Tel Aviv (IL); Netta Hendler, Tel Aviv (IL); Elad Mentovich, Tel Aviv (IL); Michael Gozin, Tel Aviv (IL); Shachar Richter, Mazkeret Batia (IL); Liron Reshef-Steinberger, Tel Aviv (IL); Roman Nudelman, Tel Aviv (IL); Tamilla Gulakhmedova, Tel Aviv (IL)

(73) Assignee: RAMOT AT TEL-AVIV UNIVERSITY LTD., Tel-Aviv (IL)

( * ) Notice: Subject to any disclaimer, the term of this patent is extended or adjusted under 35 U.S.C. 154(b) by 0 days.

(21) Appl. No.: 14/758,965

(22) PCT Filed: Jan. 7, 2014

(86) PCT No.: PCT/IB2014/058101
§ 371 (c)(1),
(2) Date: Jul. 2, 2015

(87) PCT Pub. No.: WO2014/106830
PCT Pub. Date: Jul. 10, 2014

(65) Prior Publication Data
US 2015/0335014 A1    Nov. 26, 2015

Related U.S. Application Data

(60) Provisional application No. 61/749,396, filed on Jan. 7, 2013.

(51) Int. Cl.
*A61L 15/32*    (2006.01)
*A61L 15/60*    (2006.01)
(Continued)

(52) U.S. Cl.
CPC .............. *A01N 37/18* (2013.01); *A01N 59/16* (2013.01); *A61L 15/32* (2013.01); *A61L 15/325* (2013.01);
(Continued)

(58) Field of Classification Search
CPC ........ A61K 47/42; A61L 15/32; A61L 15/325; A61L 15/40; A61L 15/60; A61L 31/044;
(Continued)

(56) References Cited

U.S. PATENT DOCUMENTS 3,632,361 A    1/1972    Battista
4,412,947 A    11/1983    Cioca
(Continued)

FOREIGN PATENT DOCUMENTS

EP    2889305    7/2015
WO    2009090655    7/2009

OTHER PUBLICATIONS

Lafontaine et al. Changes in Size and Weight of Hydromedusae During Formalin Preservation. Bulletin of Marine Science. 1989. vol. 44, No. 3, pp. 1129-1137.*
(Continued)

*Primary Examiner* — Jeffrey E Russel
(74) *Attorney, Agent, or Firm* — A.C. Entis-IP Ltd.

(57) ABSTRACT

Embodiments of the invention relate to jellyfish polymer comprising jellyfish protein and at least one additive, wherein the jellyfish protein comprises mucin and collagen. Further embodiments relate to hydrogels, antibacterial polymers, composite polymers and methods of making the polymers.

23 Claims, 7 Drawing Sheets

(51) Int. Cl.
*C08H 1/00* (2006.01)
*A01N 37/18* (2006.01)
*A01N 59/16* (2006.01)
*B01J 20/24* (2006.01)
*B01J 20/28* (2006.01)
*A61L 31/04* (2006.01)
*A61L 31/12* (2006.01)
*A61L 31/14* (2006.01)
*A61L 31/16* (2006.01)
*A61L 15/40* (2006.01)
*A61L 15/44* (2006.01)
*B82Y 5/00* (2011.01)
*C07K 14/435* (2006.01)

(52) U.S. Cl.
CPC ............... *A61L 15/40* (2013.01); *A61L 15/44* (2013.01); *A61L 15/60* (2013.01); *A61L 31/044* (2013.01); *A61L 31/047* (2013.01); *A61L 31/128* (2013.01); *A61L 31/145* (2013.01); *A61L 31/16* (2013.01); *B01J 20/24* (2013.01); *B01J 20/28047* (2013.01); *C08H 1/00* (2013.01); *A61L 2300/104* (2013.01); *A61L 2300/406* (2013.01); *A61L 2300/442* (2013.01); *A61L 2300/624* (2013.01); *A61L 2400/12* (2013.01); *B82Y 5/00* (2013.01); *C07K 14/43595* (2013.01)

(58) Field of Classification Search
CPC .... A61L 31/047; A61L 31/128; A61L 31/145; A61L 2300/104; A61L 2300/252; A61L 2400/12; B01J 20/24; B01J 20/28047; C07K 14/43595; C08H 1/00; C08H 1/02
See application file for complete search history.

(56) References Cited

U.S. PATENT DOCUMENTS

| | | | |
|---|---|---|---|
| 5,538,945 A * | 7/1996 | Pallenberg | A61K 8/19 514/20.7 |
| 5,714,582 A | 2/1998 | Wolfinbarger | |
| 6,733,651 B1 * | 5/2004 | Hoffacker | C25D 3/48 205/267 |
| 6,783,687 B2 * | 8/2004 | Richard | C02F 1/4604 204/554 |
| 7,829,679 B2 | 11/2010 | Ushida et al. | |
| 2003/0088069 A1 | 5/2003 | Su et al. | |
| 2006/0149182 A1 * | 7/2006 | Cullen | C08B 37/00 602/49 |
| 2007/0029259 A1 * | 2/2007 | Kakita | A01G 33/00 210/660 |
| 2010/0285102 A1 | 11/2010 | Angel | |
| 2011/0215716 A1 | 9/2011 | Belgorodsky et al. | |

OTHER PUBLICATIONS

Wang et al. Jellyfish gel and its hybrid hydrogels with high mechanical strength. Soft Matter. 2011. vol. 7, pp. 211-219.*
Pearson, Roger, Isolation, Biochemical Characterization and Anti-adhesion Property of Mucin from the Blue Blubber Jellyfish (*Catostylus mocaicus*) Bioscience Methods, Jun. 3, 2011, vol. 2, No. 4, pp. 21-30.
Hendler Netta, Bio-inspired synthesis of chiral silver nanoparticles in mucin glycoprotein-the natual choice, Chem. Commun., 47, Jul. 14, 2011, pp. 7419-7421.
Masuda, Akiko; Mucin (Qniumucin), a Glycoprotein from Jellyfish, and Determination of Its Main Chain Structure, 2007 American Chemical Society and American Society of Pharmacognosy, Jun. 14, 2007, pp. 1089-1092.
Belgorodsky, Bogdan; Mucin Complexes of Nanomaterials: First Biochemical Encounter, 2010 Wiley-VCH Verlag GmbH & Co. KGaA, Weinheim, pp. 262-269.
International Search Report dated May 22, 2014 for PCT/IB2014/058101 Filed Jan. 7, 2014.
European Search Report mailed Jun. 15, 2016 for corresponding EP application No. 14735450.0, filing date Jul. 22, 2015.

* cited by examiner

JELLYFISH-DERIVED POLYMER

RELATED APPLICATIONS

The present application is a US National Phase of PCT Application No. PCT/IB2014/058101, filed on Jan. 7, 2014, which claims the benefit under 35 U.S.C. §119(e) of U.S. Provisional 61/749,396 filed on Jan. 7, 2013, the disclosure of which is incorporated herein by reference.

TECHNICAL FIELD

Embodiments of the invention relate to jellyfish-derived polymers and methods of manufacture thereof.

BACKGROUND

Jellyfish are members of the phylum Cnidaria family of aquatic organisms, which typically live in salt water seas and oceans. Jellyfish consist of tentacles, which may contain stinging structures, comprising venom, and a gelatinous bell. Jellyfish tend to drift, while feeding on plankton, fish and sometimes other jellyfish. In certain locations, jellyfish tend to drift in groups consisting of large numbers of jellyfish, called blooms.

Large jellyfish blooms may be detrimental to humans. When blooms approach coastal bathing areas, jellyfish may release their venom into sea water or sting humans upon contact, often causing an unpleasant allergic reaction, which may be severe or even deadly in the case of certain jellyfish. In addition, blooms impact fishing industries, by eating commercial fish and by becoming entangled in fishing nets. Another negative impact of jellyfish blooms is clogging of industrial equipment. Jellyfish have been implicated in damage to power plants, desalination plants and ship engines that rely on sea-water intake.

Industries which rely on salt-water intake, such as power plants, may need to remove large quantities (multiple tons per day) of jellyfish from water intake systems, to ensure proper functioning of these systems. Once the jellyfish are removed, they cause an ecological problem, as they need to be disposed of and regulations often prohibit dumping them back into the sea. As a result, they require shipment to landfills for burial. Disposal is often difficult, because once jellyfish are removed from water, they begin to decay and emit an unpleasant smell.

Methods of manufacture using components of jellyfish have been disclosed in U.S. Pat. Nos. 5,714,582, and 7,829,679 and US Application Publications 2010/0285102 and 2003/0088069.

SUMMARY

Embodiments of the invention relate to jellyfish polymer comprising jellyfish protein and at least one additive, wherein the jellyfish protein comprises mucin and collagen. Optionally, mucin and collagen are present in the same proportions as in naturally occurring jellyfish. Optionally, the at least one additive is selected from the group consisting of: a filler, plasticizer, a composite-forming material, a gel-forming material, metal particles, an antibiotic agent and a coloring. Optionally, the additive is selected from the group consisting of: guar, agar, alginic acid or a salt thereof, gelatin, glycerol or hyaluronic acid. Optionally, the composite forming material is selected from the group consisting of: a nanoparticle, a carbon nanotube, a multiwalled nanotube, fullerene, a nanodot, a dye, a nanorod, a cluster compound, graphene and its derivatives, a metal cluster, a polyoxometalate cluster, a metal ion and a metal complex. Optionally, the nanoparticle is a metal nanoparticle, semiconductor nanoparticle, metal oxide nanoparticle, ceramic nanoparticle, carbon nanoparticle or carbon nanotube. Optionally, the nanoparticle is a silver nanoparticle. Optionally, the ratio between nanoparticle and jellyfish protein is between about 1:5 to about 5:1. Optionally, the nanoparticles have an average diameter of about 20-60 nanometers. Optionally, the nanoparticles have an average diameter of about 40 nanometers. Optionally, the polymer in the form of a hydrogel. Optionally the polymer comprises at least one of collagen, agarose, cellulose, gelatin, glycerol, PVA (polyvinyl alcohol), PANPS (poly(2-acrylamido-2-methylpropanesulfonic acid)), and/or PAA (poly(acrylamide)). Optionally, upon exposure to moisture, the polymer is capable of adsorbing at least 100% of its weight in water. Optionally, upon exposure to moisture, the polymer is capable of adsorbing at least 200% of its weight in water. Optionally, the polymer comprises between about 20 and about 60 percent jellyfish protein by weight. Optionally, the polymer comprises about 40 percent jellyfish protein by weight. Optionally, the polymer biodegrades up to 90% by weight in 30 days. Optionally, the polymer comprises less than 17 parts per million (PPM, by weight) Cadmium (Cd), less than 750 PPM Copper (Cu), less than 8.5 PPM Mercury (Hg) and less than 150 PPM Lead (Pb) Optionally, the polymer has a Young's modulus of between about 10 kilopascals and about 5000 megapascals.

Further embodiments of the invention relate to a sanitary hygiene apparatus comprising a polymer, the polymer comprising jellyfish protein. Optionally, the sanitary hygiene apparatus is in the form of a diaper, feminine hygienic product, bandage, medical gloves, and medical wrapping material. Optionally, the sanitary hygiene apparatus is in the form of a hydrogel. Optionally, the sanitary hygiene apparatus comprises a food wrapped in it.

Further embodiments of the invention relate to a jellyfish polymer, wherein the polymer prevents the growth of bacterial microorganisms.

Further embodiments of the invention relate to a method of manufacturing a jellyfish-derived polymer comprising isolated jellyfish protein from jellyfish and crosslinking the jellyfish protein to form a polymer or gelation of the protein to form a hydrogel. Optionally, the jellyfish-derived protein comprises mucin and collagen. Optionally, mucin and collagen are not separated from each other before the polymer formation. Optionally, at least one additive is added selected from the group consisting of: a filler, plasticizer, a composite-forming material, metal particles, an antibiotic agent and a coloring. Further embodiments of the invention relate to a jellyfish-derived polymer manufactured according to one of the aforementioned methods. Optionally, the polymer comprises polymerized mucin and collagen.

In the discussion, unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF FIGURES

Non-limiting examples of embodiments of the invention are described below, with reference to a figure attached hereto. Dimensions of components and features shown in the figures are chosen for convenience and clarity of presentation and are not necessarily shown to scale.

DETAILED DESCRIPTION

An embodiment of the invention provides a method of manufacturing polymers from jellyfish tissue. These polymers are biodegradable and may be used for a variety of industrial applications.

Methods according to embodiments of the invention are inexpensive, environmentally-friendly and allow use jellyfish tissue, thus obviating the need to dispose of collected jellyfish in landfills. Methods according to embodiments of the invention, produce little to no waste and energetically economical. Methods according to embodiments of the invention are performed in non-acidic media, making waste-disposal easier.

Two of the main proteins, which comprise jellyfish tissue, are mucin (a glycoprotein) and collagen. According to embodiments of the invention mucin and collagen are not isolated from each other, rather, polymers are formed from mixtures of these proteins. Methods of manufacture of polymers, according to embodiments of the invention, do not require separation of mucin from collagen, thereby making the methods inexpensive and are industrially viable. Isolation of jellyfish protein may be performed at room temperature, thereby decreasing the energy input, required to obtain material for formation of polymers.

Collagen is a fibrillar protein abundant in a flesh and connective tissues of many vertebrate and invertebrate life forms. Collagen can create fibrils that could be found in fibrous tissues, including tendon, ligament, skin, cornea, cartilage, bone, blood vessels, gut and intervertebral discs.

Mucins are a family of heavily glycosylated proteins with high molecular weight. Mucins are produced in many organisms and present in epithelial cells and in mucus. One of the key characteristics of mucins is their ability to form gels. Therefore, mucins are a key component in most gel-like secretions, serving functions from lubrication to cell signaling and forming chemical barriers.

In an embodiment of the invention, novel polymers comprising non-polymeric additives, for example, nanoparticles, are manufactured. These novel polymers have unique qualities and may be used for a variety of industrial applications.

In an embodiment of the invention, novel polymers comprising anti-bacterial additives are manufactured. These polymers have unique qualities and may be used for a variety of industrial applications in which antibacterial qualities may be useful including, diapers, feminine hygienic products, bandages, medical gloves, and medical wrapping materials.

Polymers manufactured according to embodiments of the invention may be used to form a medicament, an optoelectronic device, a biomedical device, a packaging material, a fiber, a fabric, a transparent sheet, a cosmetic and a construction material.

In the following detailed description, a method of manufacturing jellyfish-derived polymer is described and discussed with reference to FIG. 1.

Figure 1:
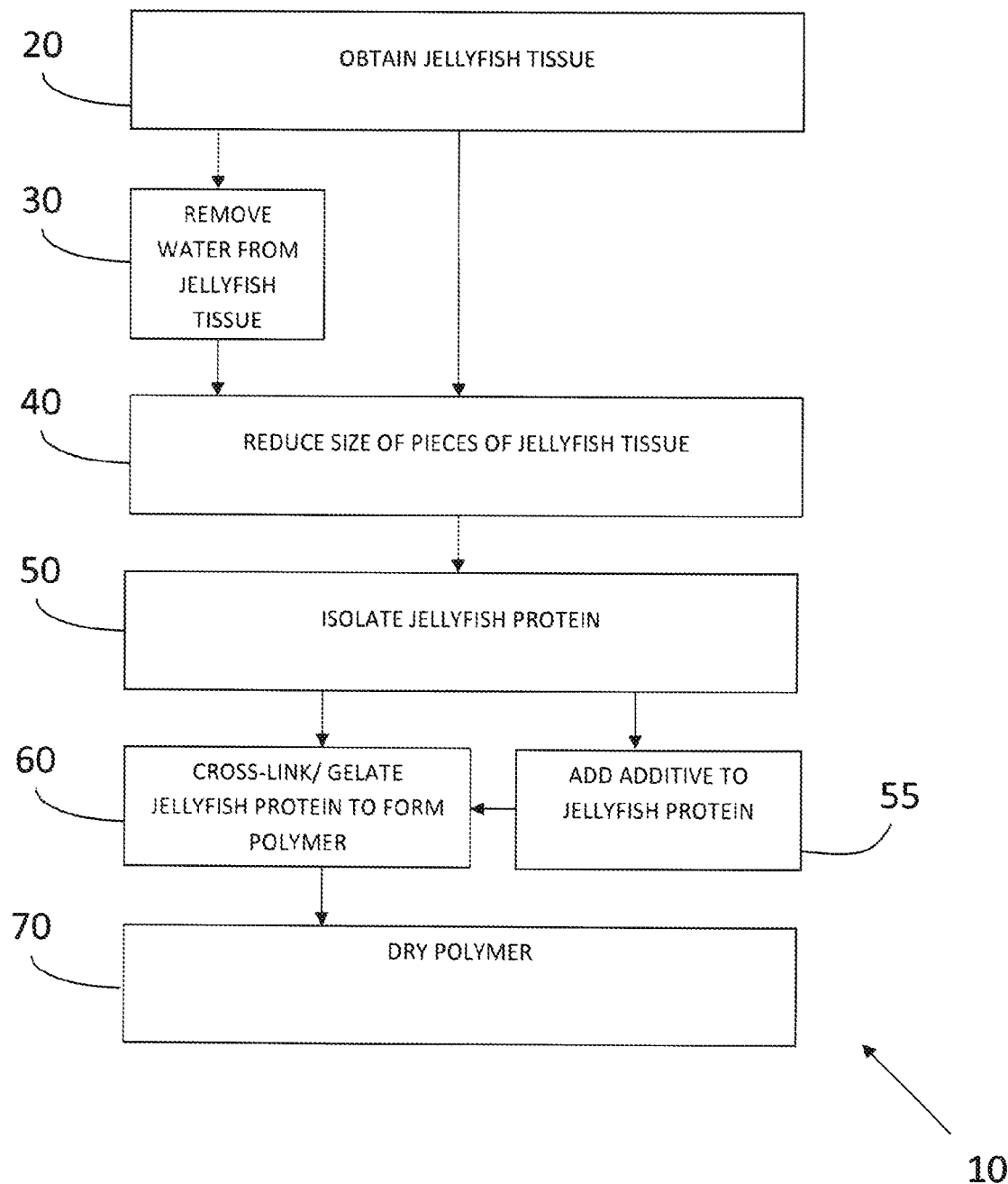
FIG. 1 schematically depicts a block flow diagram of a method of manufacturing jellyfish-derived polymer, in accordance with an embodiment of the invention.

FIG. 1 schematically depicts a block flow diagram of a Method 10 of manufacturing jellyfish-derived polymer in accordance with an embodiment of the invention.

Block 20 depicts obtaining jellyfish tissue. In an embodiment of the invention, jellyfish tissue is obtained from complete jellyfish. In an embodiment of the invention, tentacles are removed from the jellyfish, for example, by mechanical cutting, and the remaining bell is used as a source for jellyfish tissue. In an embodiment of the invention, an outer layer of the jellyfish bell is removed. In an embodiment of the invention, tentacles, gonadal material and/or digestive juices are removed. In an embodiment of the invention, jellyfish, or parts thereof, are washed to remove debris.

In an embodiment of the invention, the jellyfish used is from the Scyphozoa class. In an embodiment of the invention, the jellyfish used is from the Scyphozoa class and is of a species selected from the group consisting of: *Rhopilema nomadica, Aurelia aurita* and *Aurelia labiata*. In an embodiment of the invention, the jellyfish is selected from *Chrysaora melanaster* (brown jellyfish) (family Pelagiidae), *Aequorea coerulescens* (Owan-kurage jellyfish) (family Aequoreidae), *Nemopilema nomurai* (Echizen-kurage jellyfish) (family Stomolophidae), *Charybdea rastoni* (Andon-kurage jellyfish) (family Carybdeidae), *Rhopilema esculenta* (Bizen-kurage jellyfish) (family Rhizostomidae), and *Chiropsalmus quadrigatus* (Habu-kurage jellyfish) (family Chirodropidae).

Jellyfish tissue obtained in Block 20 may undergo water removal, as in Block 30 or may undergo size reduction as in Block 40, without prior water removal.

Block 30 depicts optionally removing water from jellyfish tissue. By removal of water from jellyfish tissue, cells of jellyfish may be ruptured. In an embodiment of the invention, water is removed by adding salt to jellyfish tissue. In an embodiment of the invention, the salt is an aluminum sulfate salt. In an embodiment of the invention, the aluminum sulfate salt is potassium aluminum sulfate. After application of salt to jellyfish tissue, the tissue may be left to dry on drying racks or may be subjected to physical pressure. Salt may be applied to jellyfish tissue multiple times to enhance drying. Salt also has a preservative effect, which prevents jellyfish from decaying and emitting odor. In an embodiment of the invention, the salt is subsequently removed by washing.

In an embodiment of the invention, removing water from jellyfish tissue is accomplished by applying physical pressure to the tissue. In an embodiment of the invention, water is removed using a French pressure cell press. In an embodiment of the invention, the pressure in the French pressure cell press is about 1,000 pounds per square inch.

In an embodiment of the invention, water is removed using a freeze-thaw process, in which jellyfish tissue is frozen and thawed, to rupture cell membranes. In an embodiment of the invention, the freeze-thaw process is repeated 3-5 times.

In an embodiment of the invention, water is removed through lyophilization.

In an embodiment of the invention, ozone is used to remove water from jellyfish tissue. In an embodiment of the invention, ozone is added to jellyfish tissue in an amount ranging from about 0.2% to 10% by weight. Ozone also has a preservative effect which prevents jellyfish from decaying and emitting odor.

In an embodiment of the invention, in Block 30, water is partially removed from the jellyfish, and there remains some water within the jellyfish.

Block 40 depicts reducing size of pieces of jellyfish tissue. In Block 40, dried or non-dried jellyfish tissue may be used. In an embodiment of the invention, size reduction is performed using a blender. In an embodiment of the invention, size reduction is performed using a homogenizer. In an embodiment of the invention, the average diameter of jellyfish tissue pieces is less than about 2 millimeters (mm) In an embodiment of the invention, a homogenizer is used and cell lysis may occur. In an embodiment of the invention, a homogenized solution or suspension is formed upon size reduction of pieces of jellyfish tissue. In an embodiment of the invention, the homogenized solution or suspension is separated from pieces of jellyfish tissue, for example, by filtration.

Block 50 depicts isolating jellyfish protein. In an embodiment of the invention, jellyfish tissue of Block 40, either in solid form, or in the form of a solution or suspension, may be added to a solvent, and solids (comprising jellyfish protein) may be removed from the solvent using application of pressure, application of vacuum, filtration, centrifugation, lyophilization or a combination of two or more thereof, resulting in solid jellyfish protein.

In an embodiment of the invention, in which jellyfish tissue of Block 40 is added in the form of a solution or suspension, in Block 50 a solvent is added, in which jellyfish protein is insoluble, thereby causing sedimentation of jellyfish protein. In an embodiment of the invention, the solvent and/or water is separated from the solid jellyfish protein, and the solvent is removed or evaporated, leaving behind solid jellyfish protein.

In an embodiment of the invention, the solvent is a water-soluble organic solvent. In an embodiment of the invention, the water-soluble organic solvent is an alcohol. In an embodiment of the invention, the water-soluble organic solvent comprises ethanol. In an embodiment of the invention the solvent is water, a hypotonic or a hypertonic (relative to jellyfish tissue) aqueous solution. In an embodiment, the solution is an aqueous buffer.

In an embodiment of the invention, the ratio of solvent to jellyfish tissue or solution or suspension is from about 1:3 to about 100:1. In an embodiment of the invention, the solvent is added in a ratio of about three parts solvent to one part jellyfish tissue or solution or suspension.

In an embodiment of the invention, after the solvent is removed from the jellyfish protein, it is reused to add to additional jellyfish tissue.

In an embodiment of the invention, isolated jellyfish protein comprises mucin and collagen. In an embodiment of the invention isolated jellyfish protein comprises mucin and collagen in a ratio similar to the ratio of mucin and collagen present in whole jellyfish tissue.

In an embodiment of the invention, isolated solid jellyfish protein is a mixture of proteins, further comprising relatively small quantities of other jellyfish-derived compounds, such as fats or amphiphilic compounds.

Block 55 comprises optionally adding an additive to jellyfish protein. In an embodiment of the invention, the additive is a member selected from the group consisting of: a filler, a gel forming agent, a crosslinking agent, a plasticizer, a composite-forming material and a coloring. In an embodiment of the invention, the gel forming agent or crosslinking agent additive is guar, agar, alginic acid or a salt thereof, gelatin or hyaluronic acid. In an embodiment of the invention, the additive is glycerine. In an embodiment of the invention, the composite-forming material is a material selected from the group consisting of: a nanoparticle. a carbon nanotube, a multiwalled nanotube, fullerene, a nanodot, a dye, a nanorod, a cluster compound, graphene and its derivatives, a metal cluster, a polyoxometalate cluster, a metal ion and a metal complex. In an embodiment of the invention, the nanoparticle is a metal nanoparticle, semiconductor nanoparticle, metal oxide nanoparticle, ceramic nanoparticle, carbon nanoparticle or carbon nanotube. According to an embodiment of the invention, the metal or nanoparticle comprises copper, silver and/or gold. In an embodiment of the invention, a monomer or an oligomer is added, which upon polymerization conducts electric charge. In an embodiment of the invention a drug is carried by the jellyfish protein. The composite material may be an antibacterial or disinfectant agent such as cetyltrimethylammonium bromide.

In an embodiment of the invention, jellyfish protein is added to a buffered solution, before addition of the additive. In an embodiment, the buffered solution is a sodium phosphate buffer solution. In an embodiment of the invention, the pH of the buffered solution is about 7. In an embodiment of the invention, the pH of the buffered solution is about 9.

Block 60 depicts gel formation or crosslinking jellyfish protein to form a polymer. Crosslinking can be achieved through physical or chemical methods or combinations thereof. In an embodiment of the invention, crosslinking is achieved through application of heat, pressure, irradiation or a combination thereof to jellyfish protein. In an embodiment of the invention, crosslinking is performed by passing jellyfish protein through an extruder.

According to embodiments of the invention, a polymer is formed that is a copolymer, comprising many protein molecules and/or amino acids derived from jellyfish. The protein and/or amino acid molecules may be from separate sections of jellyfish which are physically separated, then bound to each other through a variety of agents to form copolymers. The copolymers may be grafted copolymers or block copolymers.

In an embodiment of the invention, a crosslinking agent or gel forming agent is added in the Block 60. In an embodiment of the invention, the crosslinking agent is a peptide, an amino acid, a DNA, a RNA, a PNA (protein nucleic acid), a protein, hyaluronic acid, guar, a chitosan polysaccharide, dialdehydes, polyaldehydes, isocyanates, diisocyanates, polyisocyanates, thiocyanates, dithiocyanates, polythiocyanates, diacylhalides, polyacylhalides, dianhydrides, polyanhydrides, dithiols or polythiols. In an embodiment of the invention, the ratio of crosslinking agent to jellyfish protein is about 1:200 to about 10:1.

In an embodiment of the invention, a hydrogel, preferably a crosslinked hydrogel, is formed by adding an agent such as collagen, agarose, cellulose, gelatin, agar, alginic acid or a salt thereof, hyaluronic acid, PVA (polyvinyl alcohol), PANPS (poly(2-acrylamido-2-methylpropanesulfonic acid)), and/or PAA (poly(acrylamide)) is added in Block 60. A crosslinking agent, such as MBAA (N—N'-methylene-bis-acrylamide) and/or oxoglutaric acid may be added. In an embodiment of the invention, the mixture is then incubated for about 24 hours. In an embodiment of the invention, the mixture is irradiated for about 2 hours.

In an embodiment of the invention, a double crosslinked polymer is formed. A cross-linked hydrogel may be immersed in a second solution comprising a crosslinking agent for another 24 hours, to form a double crosslinked hydrogel.

In an embodiment of the invention, the polymer comprises a composite forming material and is used for the manufacture of a medicament, an optoelectronic device, a biomedical device, and/or a packaging. Methods of manufacture of composite polymeric materials are described in US patent application 2011/0215716, incorporated herein by reference.

Block 70 depicts drying the polymer. In an embodiment of the invention, the polymer is dried under vacuum conditions. In an embodiment of the invention, the polymer is dried by exposure to heat, to allow evaporation of solvent. In an embodiment, the polymer is dried by lyophilization.

Jellyfish derived polymer prepared according to embodiments of the invention is biodegradable and has physical properties appropriate to be used for a variety of applications.

Example 1

Isolation of Jellyfish Protein

*Rhopilema nomadica* jellyfish were collected from the shore and from the sea in Tel Aviv, Israel. Jellyfish were washed in cold water, and tentacles were removed. The jellyfish were cut into pieces and blended in a blender for approximately 3 minutes. The blend was filtered and separated into a liquid solution/suspension and gel-like material using a coarse strainer, having holes approximately 1 mm in size.

Gel-like material which remained in the strainer was washed by combining with 3 volumes of ethanol for two hours, centrifuged at 4° C. for 15 minutes at 10,000 g (gravitational accelerations) to remove residual water and ethanol under vacuum, then transferred to a rotary evaporator for 8 hours, and then subjected to a higher vacuum for overnight. The remaining solid was lyophilized and then frozen. The jellyfish protein was designated a Batch A.

The liquid which was removed from the strainer was added to 3 volumes of ethanol, transferred to cold storage and subjected to centrifugation at 4° C. for 15 minutes at 10,000 g. The solids were then lyophilized and frozen. The batch of jellyfish protein was designated as Batch B.

Another batch of *Rhopilema nomadica* was collected from the sea in Tel Aviv, Israel. Jellyfish were washed in cold water, and tentacles were removed. The jellyfish were cut into pieces and blended in a blender for approximately 3 minutes. The mixture was refrigerated overnight with about 80% by volume ethanol. The mixture was then dried in an evaporator, with some liquid remaining. The batch of jellyfish protein was designated as batch C.

Example 2A

Polymer Formation

Polymers were formed from protein Batch A and Batch B, using the following general procedure: Jellyfish protein is mixed with a buffer solution (phosphate buffer), diluted to a concentration of 2 millimolar (mM) and stirred overnight. Guar (Sigma-Aldrich) was then added gradually, while mixing by hand. The material was then transferred to a nonstick sheet or mold, having a silicon or Teflon coating. The material was then dried under a hood for about 48 hours, to form a dried polymer.

The polymer batches in Table 1 below were prepared by using either protein Batch A or Batch B, as described, but with process changes, according to the details in the table. The $AgNO_3$ solution used in Batch 11 (Table 1) was prepared by mixing 10 milligrams (mg) of $AgNO_3$ in 1 milliliter (ml) of $H_2O$.

TABLE 1

| Polymer Batch | Protein Batch | Protein quantity (milligram) | Additive | Additive quantity (milligram) | pH/amount of solution (milliliter) | Properties |
|---|---|---|---|---|---|---|
| 1 | A | 99.8 | Guar | 50.9 | 7.2/1.5 | Elastic like plastic bag, easily breakable |
| 2 | A | 100.2 | Guar | 75 | 7.2/1.5 | Less elastic than Batch 1 |
| 3 | A | 100.2 | Guar | 100.2 | 7.2/1.5 | Strong bioplastic |
| 4 | B | 100.3 | Guar | 50.6 | 7.2/1.5 | Strong, elastic |
| 5 | B | 101.8 | Guar | 75.8 | 7.2/1.5 | Brittle |
| 6 | B | 100.8 | Guar | 101.1 | 7.2/1.5 | Slightly brittle |
| 7 | B | 100.1 | Guar | 100.3 | 3.6/1.5 | Elastic, rubbery |
| 8 | A | 100.2 | Guar | 101.7 | 3.6/1.5 | A little bit elastic |
| 11 | B | 120.0 | $AgNO_3$ | 0.15 ml of $AgNO_3$ solution | 10.0/1.5 | — |
| 12 | A | 239.8 | Guar | 119.8 | 7.2/2 | Elastic like plastic bag, easily breakable |
| 13 | A | 239.6 | Guar | 240.6 | 7.2/2 | Strong bioplastic |
| 14 | B | 240.2 | Guar | 120.8 | 7.2/4 | Strong bioplastic, more elastic than Batch 13 |
| 15 | B | 239.5 | Guar | 240.4 | 3.6/4 | Elastic like rubber |

TABLE 1-continued

| Polymer Batch | Protein Batch | Protein quantity (milligram) | Additive | Additive quantity (milligram) | pH/amount of solution (milliliter) | Properties |
|---|---|---|---|---|---|---|
| 16 | A | 240.5 | Guar | 120.3 | 7.2/4 | Flexible but not elastic. Relatively strong. |
| 17 | A | 119.2 | Guar | 1201.5 | 7.2/20 | Strong bioplastic |
| 18 | A | 1201.6 | Guar | 599.8 | 7.2/20 | Elastic like plastic bag, easily breakable; presence of large fibers |
| 19 | B | 1200.0 | Guar | 601.0 | 7.2/20 | Similar to batch 14 |
| 20 | A | 360 | Guar | 270 | 7.2/20 | Less elastic than batch 1 |
| 21 | B | 1201.1 | Guar | 1200.0 | 3.6/20 | Similar to batch 15 |
| 22 | A | 1198 | Guar | 600.5 | 7.2/20 | Similar to batch 18 |

Additional samples were made using a similar process with jellyfish protein, agar, alginate Na, gelatin and combinations thereof. Those without jellyfish protein were made as "reference" samples for comparison:

TABLE 2

| Sample | Jellyfish Protein | Agar | Alginate Na | Gelatin | Water | pH |
|---|---|---|---|---|---|---|
| 168 (reference) | 0 | 0.3 gram (g) | 0 | 0 | 16.5 ml | ~6 |
| 174 (reference) | 0 | 0 | 0.3 g | 0.6 g | 15 ml | ~6 |
| 154 (reference) | 0 | 0 | 0.3 | 0 | 15 ml | ~6 |
| 155 (reference) | 0 | 0 | 0.3 g | 0.6 g | 15 ml | ~6 |
| 164 (reference) | 0 | 0 | 0 | 1.5 g | 33 ml | ~6 |
| 165 (reference) | 0 | 0 | 0 | 1.8 g | 49.5 ml | ~6 |
| 166 (reference) | 0 | 0 | 0.3 g | 0 | 16.5 ml | ~6 |
| 173 | 1.425 g | 0.075 g | 0 | 0 | 10 ml | 4 |
| 169 | 1.35 g | 0.15 g | 0 | 0 | 5 ml | 4 |
| 170 | 1.2 g | 0.3 g | 0 | 0 | 8 ml | 4 |
| 177 | 1.2 g | 0.3 g | 0 | 0 | 15 ml | 9 |
| 178 | 1.2 g | 0.3 g | 0 | 0 | 15 ml | 7 |
| 175 | 1.8 g | 0 | 0.3 g | 0.6 g | 13.8 ml | ~6 |

Example 2B

Hydrogel Formation

Hydrogels may be formed from jellyfish protein according to embodiments of the invention. Hydrogels according to embodiments of the invention may have highly adsorbent properties and may be used in a variety of applications.

A procedure used for preparing jellyfish protein-containing hydrogel was: Dissolving agarose and/or gelatin at a temperature of 80° C. Jellyfish protein was mixed with glycerin and added to the hot agar solution. The mixture was then homogenized and poured into a form. The wet mixture was allowed to dry under a hood to evaporate water, at room temperature.

Gelatin was commercially available Kosher Bovine Gelatin, provided by Williger Delicatesse, Israel. Jellyfish protein was prepared according to batch B, above. In some samples, jellyfish protein in the form of gel was used, which comprised about 90% water. In some batches, dried jellyfish protein was used.

Methods for preparing hydrogel according to embodiments of the invention included the following ratios of ingredients:

Batches were prepared according to specific methods described in table 3.

TABLE 3

| Batch | Ingredients | Process | Result |
|---|---|---|---|
| HG9 | 1.2 g jellyfish protein in gel form, batch B<br>0.1 g Alginate Na<br>4.2 ml water | Homogenized. Mixture split into two parts. One part was heated to 60-70° C. while mixing for about 3-5 minutes until a homogenous solution formed. Second part not heated. Cooled overnight | Brittle but strong plastic, matte colored, not homogenous in appearance |
| HG10 | 0.25 g gelatin<br>0.75 g jellyfish protein gel, batch B<br>4.5 ml water | Homogenized. Mixture split into two parts. One part was heated to 60-70° C. while mixing for about 3-5 minutes until a homogenous solution formed. Second part not heated. Cooled overnight | |
| HG11 | 0.2 g gelatin<br>0.6 g jellyfish protein gel, batch B<br>0.1g alginate Na<br>4.6 ml water | Homogenized. Mixture split into two parts. One part was heated to 60-70° C. while mixing for about 3-5 minutes until a homogenous solution formed. Second part not heated. Cooled overnight | Non-heated part was very strong with a few bubbles and grains but improved homogeneity. Heated part was not homogeneous. |
| HG12 | 202.5 mg gelatin<br>70.3 mg dry lyophilized jellyfish protein, batch B | Homogenized. Mixture split into two parts. One part was heated to 60-70° C. while | Non-heated part was of similar strength as HG11, but had a |

TABLE 3-continued

| Batch | Ingredients | Process | Result |
|---|---|---|---|
| | 99.3 mg Alginate Na<br>5 ml water | mixing for about 3-5 minutes until a homogenous solution formed. Second part not heated. Cooled overnight. | rougher texture. Heated part was similar to HG11 but less homogenous. |
| HG13 | 202.8 mg gelatin<br>140 mg of dry jellyfish protein, batch B,<br>100.5 mg Alginate Na | Homogenized. Mixture split into two parts. One part was heated to 60-70° C. while mixing for about 3-5 minutes until a homogenous solution formed. Second part not heated. Cooled overnight. | Heated part was similar to HG11 in strength, was similar to HG12 in homogeneity. Non-heated part was similar to non-heated HG12, but with more bubbles and granules. |
| HG16 | 0.6973 g jellyfish protein,<br>0.2006 g gelatin<br>0.100 g alginate Na.<br>1.0375 g water<br>2.468 g glycerol<br>0.0983 g poly(acrylic acid), 35% solution<br>1.012 g 5% solution of Al acetylacetonate in ethyl acetate acid | Sample prepared in a silicon baking mold. Heated on a hot plate for 10 minutes at 75° C. Mixed using a spatula | Slightly shaky and difficult to remove from the mold |
| HG17 | 0.6031 g jellyfish protein,<br>0.2007 g gelatin<br>0.1102 g alginate Na.<br>0.5 g water<br>0.6061 g glycerol<br>0.0316 g chitosan<br>1.012 g 5% solution of Al acetylacetonate in ethyl acetate acid | Sample prepared in a silicon baking mold. Heated on a hot plate for 10 minutes at 75° C. Mixed using a spatula | rubbery hydrogel, not too homogenous |
| HG41b | Agarose 2%<br>Water 38%<br>Jellyfish protein 40%<br>Glycerol 20% | Agarose/gelatin was dissolved in water at a temperature of 80° C. Jellyfish was mixed with glycerin and added to the hot agar solution. The mixture was homogenized and poured into a form. | Gel like, moist |
| HG36b | Gelatin 10%<br>Water 30%<br>Jellyfish protein 40%<br>Glycerol 20% | Agarose/gelatin was dissolved in water at a temperature of 80° C. Jellyfish was mixed with glycerin and added to the hot agar solution. The mixture was homogenized and poured into a form. | Gel like, moist. |

Example 2C

Preparation of Antibacterial Polymers

Antibacterial polymer comprising jellyfish protein C was produced using the following method. An aqueous solution comprising jellyfish protein and AgNO3 in weight ratios of 2:1, 3:1, 4:1 and 5:1 in deionized water was stirred for 2 hours in dark at room temperature. Borate buffer having a pH of 9 was added, and the mixture was stirred until color changed from white to appropriate brown color for the residue, which is an indication of presence of colloidal silver. This process took about 72-96 hours. Reaction was monitored by testing for presence of Ag+ ions in the reaction solution.

All batches having weight ratios of Jellyfish Protein to AgNO3 of 2:1, 3:1, 4:1, and 5:1 of each resulted in silver nanoparticle (NP) formation within the jellyfish protein. The protein-NP complex settled as a brownish residue on the bottom of the Erlenmeyer flask (while the rest of the solution contained clear liquid.) Gravity filtration was used to separate the residue from water.

Characterization of Jellyfish protein combined with silver NP was done by Environmental Scanning Electron Microscopy (ESEM) imaging in Quanta 200 FEG ESEM on minimum magnification of ×600 and maximum ×28000. Dry and liquid samples of JFM+Ag Np and raw jellyfish for reference were scanned under various magnifications. Elemental analysis was performed on samples. The silver NP in jellyfish protein were seen through microscopy (from a batch having a 5:1 ratio) to have average size distribution around 40 nanometers (nm) while some larger aggregates with variable sizes were also observed. Although the exact shape of NP was difficult to determine, round, spherical, and rod shape particles along with bigger shapeless aggregates were observed. Ag NP were seen to cover large surface areas of jellyfish protein when compared to microscopy of jellyfish protein which did not undergo introduction of Ag NP. Elemental analysis showed that Ag NP was dispersed in even, homogenous ratios over the jellyfish protein The reduction of AgNO3 in jellyfish protein was performed without any external chemical reducers as NaBH4 or citric acid, as the reduction was carried out by the jellyfish protein itself. Reactions were pH dependent. Acidic conditions of pH 3-5 proved to produce undesired results, as grey residue instead of brown NPs appeared. Basic conditions of 9-10 PH were found as most effective for Ag NP formation. After 24 hours of stirring, color of jellyfish protein started to change from white to pale brown. After an additional 48 hours, jellyfish protein turned to a full dark brown color. At the suspected end of the reaction, an analytical counter ion test was performed to the reaction medium to show no presence of ion and no white precipitate was observed, indicating that reaction was finished and that jellyfish protein had absorbed and reduced Ag+ ions to Ag NP. In all ratios except 2:1 and 3:1 full conversion to NPs of Ag ions was observed. Without being bound by theory, it is suggested that certain proteins from the mucin family are responsible for the reduction process while other proteins act as capping agents that prevent from Ag NP to create aggregates.

After the completion of the reaction the jellyfish protein complex containing Ag NP (brown residue) was easily separated from the clear and transparent solution and stored in for more than 90 days without any visible degradation.

Example 3

Elemental Analysis

Elemental analysis was performed on samples from polymer batch HG41 using a Thermo Flash EA 1112 Elemental Analyzer. The tests were repeated in triplicate and the average elemental content, in units of percent per weight, is shown in the table below:

| Element | Test sample 1 | Test sample 2 |
|---------|---------------|---------------|
| N | 0.856 | 0.668 |
| C | 20.617 | 20.734 |
| H | 7.691 | 7.875 |
| S | 1.023 | 0.205 |

Example 4

Heavy Metal Analysis

Heavy metal analysis was performed by Bactochem Ltd., Ness-Ziona, Israel. Samples from jellyfish protein batches were tested according to ISO 11885 (ASTM D 6400). The results are summarized in table 4 below. Presence of the metals cadmium (Cd), chromium (Cr), copper (Cu), mercury (Hg), nickel (Ni), lead (Pb) and zinc (Zn) were tested and are shown, in terms of milligrams per kilogram (mg/kg) of dry material.

| Metal | A | B | C |
|-------|------|------|------|
| Cd | <0.2 | <0.2 | <0.2 |
| Cr | 1 | 0.339 | <0.3 |
| Cu | 2.8 | 1.24 | 0.845 |
| Hg | <0.5 | <0.5 | <0.5 |
| Ni | 0.8 | <0.5 | <0.5 |
| Pb | <0.5 | <0.5 | <0.5 |
| Zn | 10.7 | 6.12 | 5.4 |

All samples of polymers were found to have heavy metal levels below acceptable ranges (according to US and Israeli standards) for food-grade applications. Although jellyfish are sea creatures which may come in contact with heavy metals and may absorb heavy metal atoms in their biological tissue, polymers manufactured according to embodiments of the invention, did not have significant amounts of heavy metals and are acceptable for use in food-grade applications.

Example 5A

Testing of Mechanical Properties; Stress Strain Testing

Testing of mechanical properties (stress-strain tests) was conducted with Kammarath & Weiss tensile/compression module. Samples prepared from batch 174 (reference) and 175 were prepared and tested. Samples were casted in a standard bone-type structure and inserted in the calibrated stress-strain machine which measured the strain as a function of controlled elongation. Dry and wet hydrogel samples were tested. After testing, the fracture structure was inspected by environmental scanning electron microscopy. Young's modulus was calculated for each sample. Samples had a thickness of 0.16 mm, width of 10.7 mm and length of 50 mm.

Figure 2A:
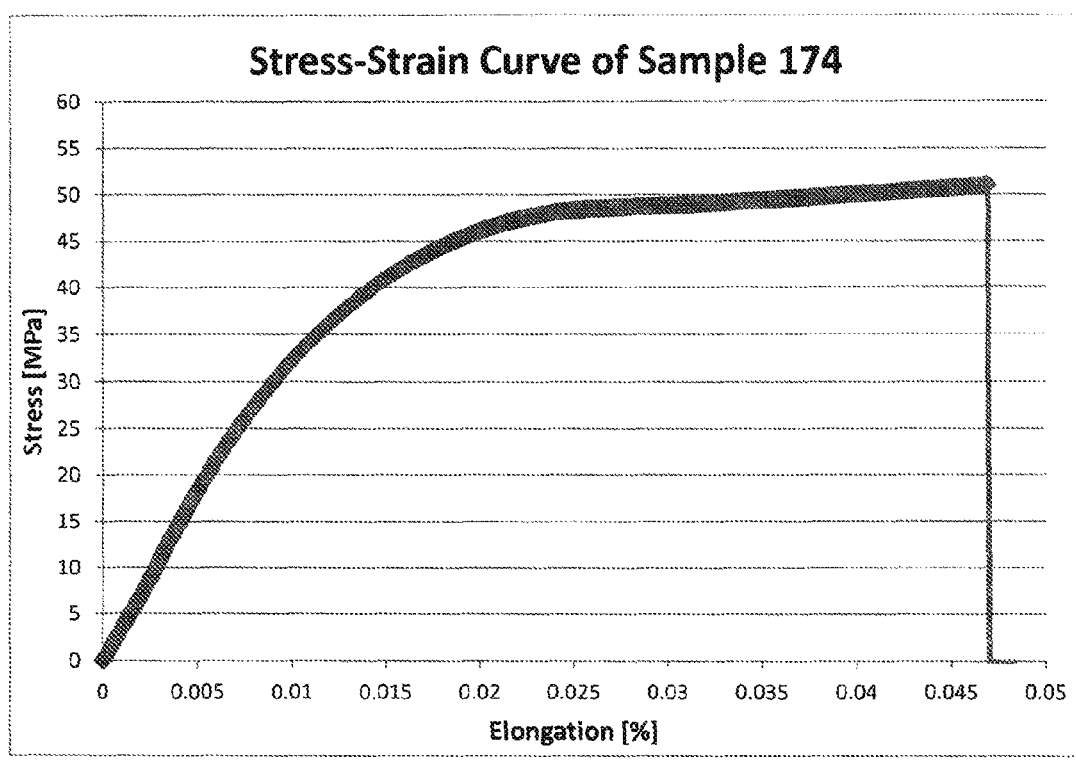
FIGS. 2A and 2B show stress-strain curves of a sample of reference batch 174 and of batch 175 in values of stress (megapascals) versus percent elongation.
Figure 2B:
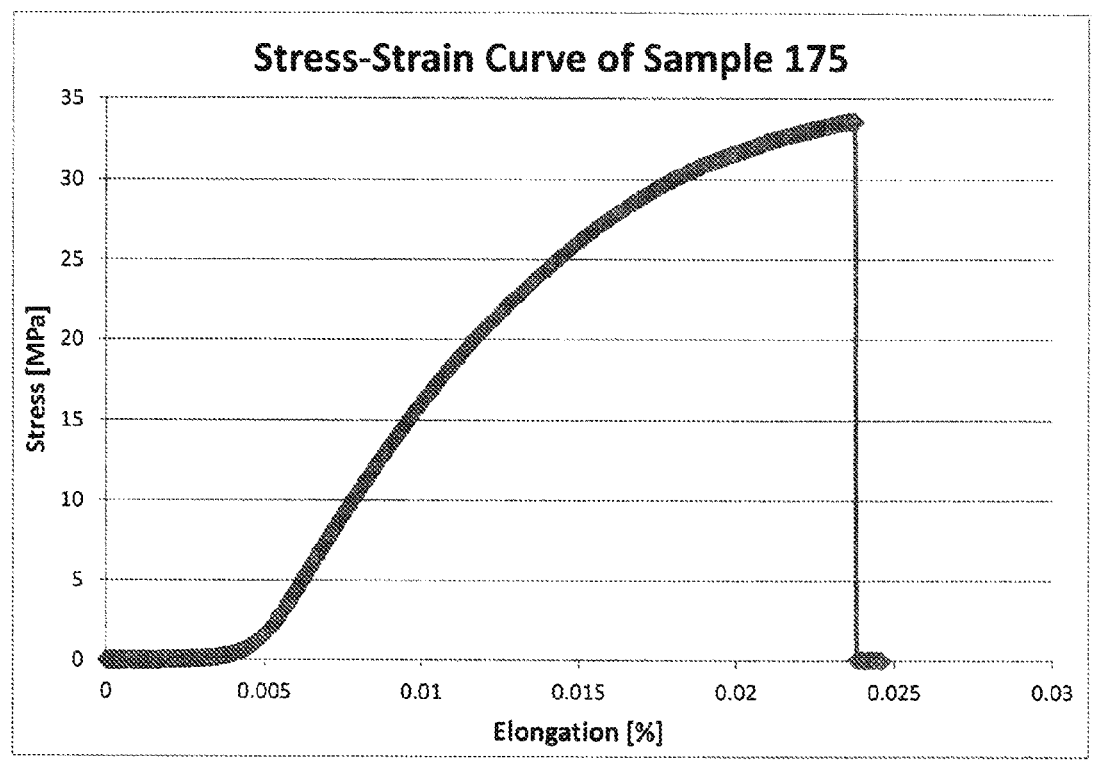

Stress-strain curves of a sample of reference batch 174 and of batch 175 are shown in FIGS. 2A and 2B respectively. Stress, in units of megapascals (MPa) is calculated relative to percent elongation and shown in the graphs for each sample.

The Young's modulus was calculated for each sample and was determined to be 3584 MPa for sample 174 and 2275 MPa for sample 175. A lower Young's modulus indicates a higher elasticity of the polymer. Stress-strain curves of hydrogels were also calculated for batches HG36b and HG41b. The Young's modulus was shown to be 17.3 and 36.0 kilo pascal (kPa) respectively. This example indicates that hydrogel elasticity can be controlled by using various methods according to embodiments of the invention.

Example 5B

Testing of Mechanical Properties; Differential Scanning Calorimetry

Figure 3:
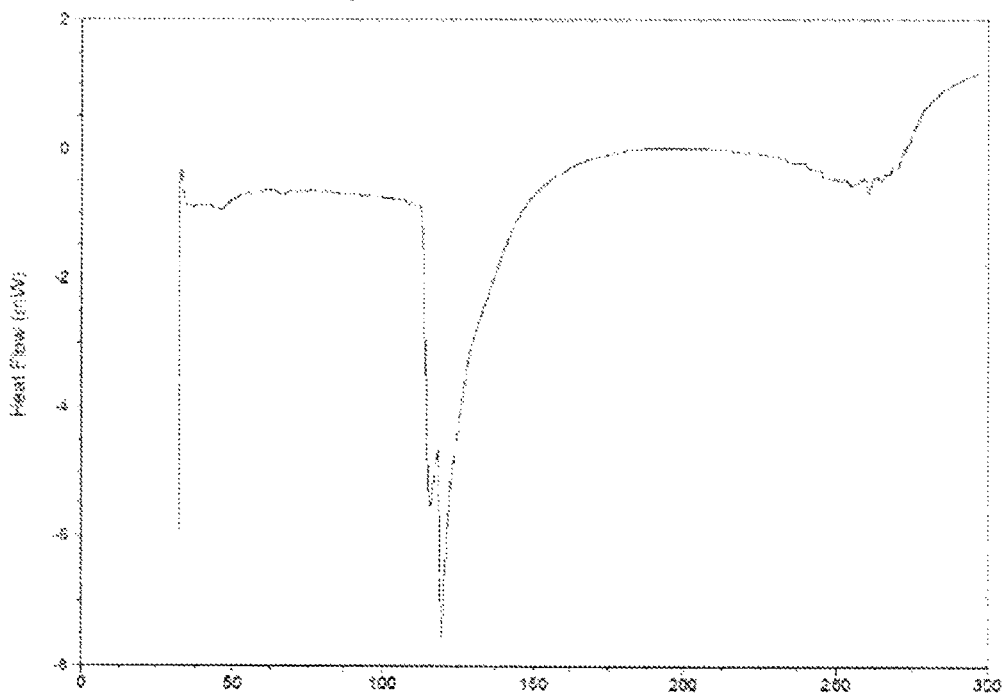
FIG. 3 shows a graph depicting differential scanning calorimetry of a sample of jellyfish protein-based hydrogel portraying heat flow in units of milliwatt (mW), versus temperature in Celsius.

Samples from batch HG36 were tested using Differential Scanning calorimetry DSC Q20, TA Instrument at heating rate 5° C./minute. Results are shown in FIG. 3, which shows a graph portraying heat flow in mW, versus temperature in Celsius.

As shown in the graph in the figure, a phase transition is seen at 120° C. and at 250° C., indicating that the sample is stable at temperatures until 120° C.

Example 5C

Testing of Mechanical Properties; Thermogravimetric Analysis

Figure 4A:
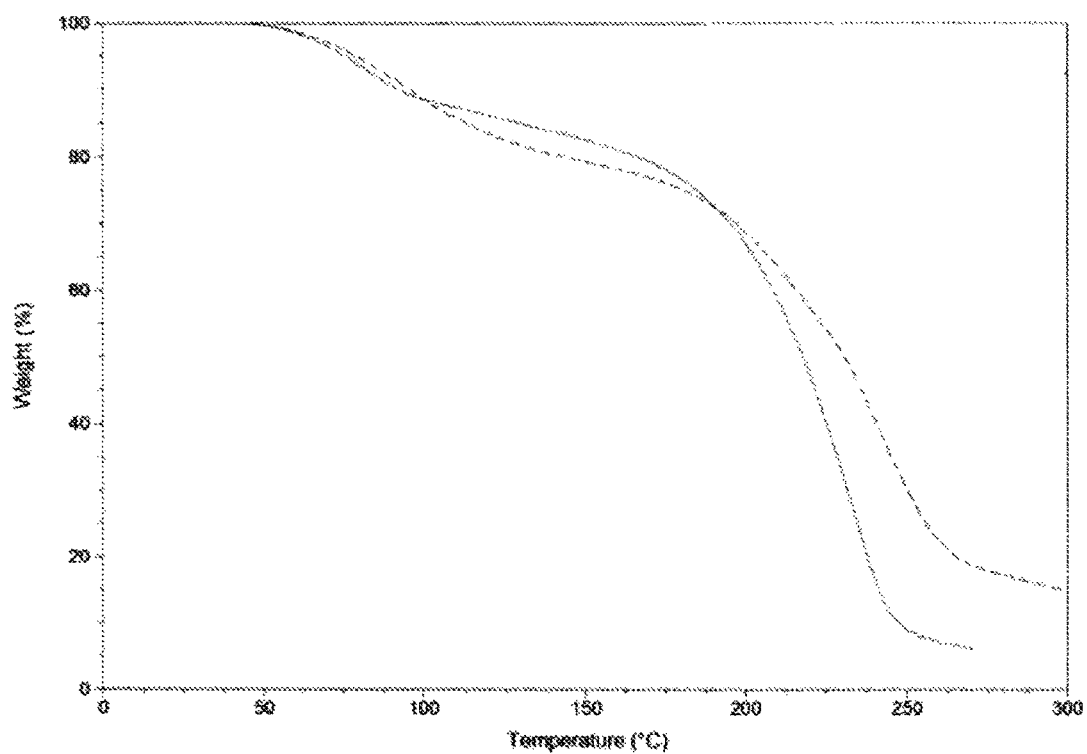
FIGS. 4A and 4B show graphs depicting thermogravimetric analysis for two samples of jellyfish-protein based hydrogel versus hydrogel without jellyfish, showing weight change as temperature is increased for two samples (4A) and the derivative of weight change (4B) as temperature is increased for the two samples.

Thermogravimetric Analysis (TGA) was performed using a research grade TGA Q5000 IR, TA Instruments at a heating rate of 5° C./minute under inert atmosphere. Two experiments were performed. In the first experiment, a batch of HG41 jellyfish protein hydrogel (dotted line) was tested compared to batch HG38 (solid line), a similar hydrogel batch, but without jellyfish protein. As can be seen from the graph in FIG. 4A, which shows weight change as temperature increases, hydrogel from batch HG41 is stable at higher temperatures than the batch without jellyfish protein.

Figure 4B:
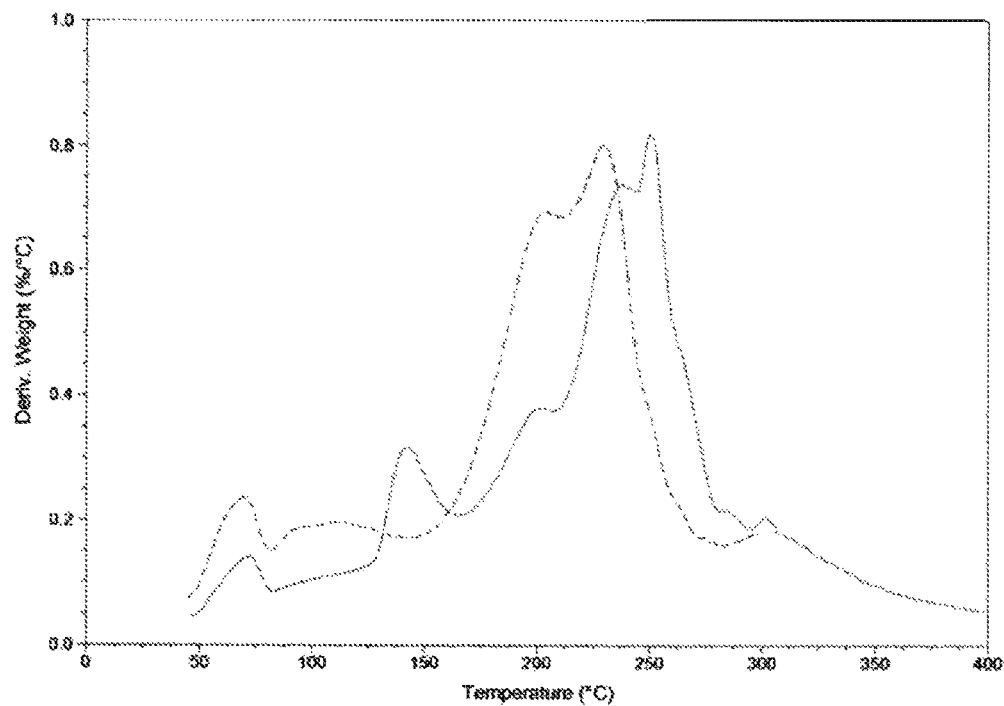

In the second experiment, a sample of hydrogel containing jellyfish protein from batch HG36 (solid line) was compared to a batch of HG39 (dotted line) which comprised a hydrogel without jellyfish protein. FIG. 4B shows the derivative of weight change as temperature is increased for the two samples. The results indicate that hydrogel samples are stable until about 200° C. and that hydrogel samples comprising jellyfish protein are more stable than their counterparts made without jellyfish protein.

Example 5D

Testing of Mechanical Properties; Morphology

Morphology of samples was examined using a scanning electron microscope (SEM) system FEI Quanta 200FEG ESEM.

Example 5E

Testing of Mechanical Properties; Swelling

Swelling testing of samples from batch HG36b was carried in a humidity chamber at room temperature and relative humidity of 99%. The swelling percentage was determined by calculating the weight of the sample after fixed intervals of time in the humidity chamber. The percentage increase is calculated as (weight at a time interval (Wt) minus initial weight ($W_0$)/initial weight ($W_0$), and is expressed in percentage. Hydrogels comprising agarose and gelatin (without jellyfish protein) were tested under the same conditions.

Figure 5:
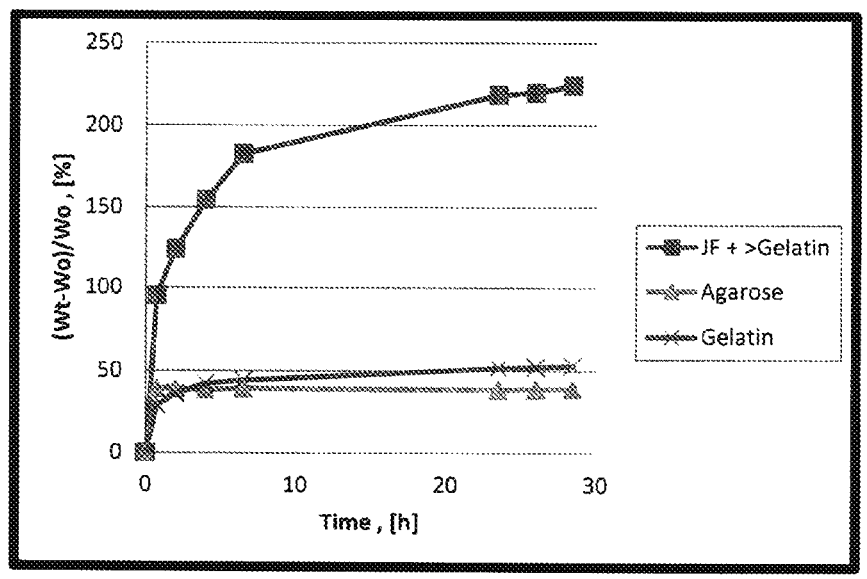
FIG. 5 shows a graph depicting swelling of a sample of jellyfish-protein based hydrogel versus hydrogels without jellyfish protein over time in the presence of humidity, illustrating the adsorbent capability of jellyfish protein-based hydrogel.

FIG. 5 shows that hydrogels according to embodiments of the invention, are effective in absorbing large amounts of moisture, to a greater extent than similar hydrogels which comprised agarose and/or gelatin, without jellyfish protein.

This example indicates that jellyfish protein according to embodiments of the invention, may be combined with fabric, such as non-woven fabric, to form bandages, feminine hygiene products, diapers and other applications in which moisture absorption is used.

According to an embodiment of the invention, hydrogels comprising jellyfish protein are capable of water absorption of at least 200%.

According to an embodiment of the invention, hydrogels comprising jellyfish protein are capable of absorbing biological floods, for example blood or urine.

Example 6

Biodegradation Testing

Biodegradation testing was performed according to the standard ISO 14855-2:

"Determination of the ultimate aerobic biodegradability of plastic materials under controlled composting conditions—Method by analysis of evolved carbon dioxide," hereby incorporated by reference, using an MODA6 (Microbial Oxidative Degradation Analyzer) Saida, Japan. A sample from batch HG41b was used for this test.

Figure 6:
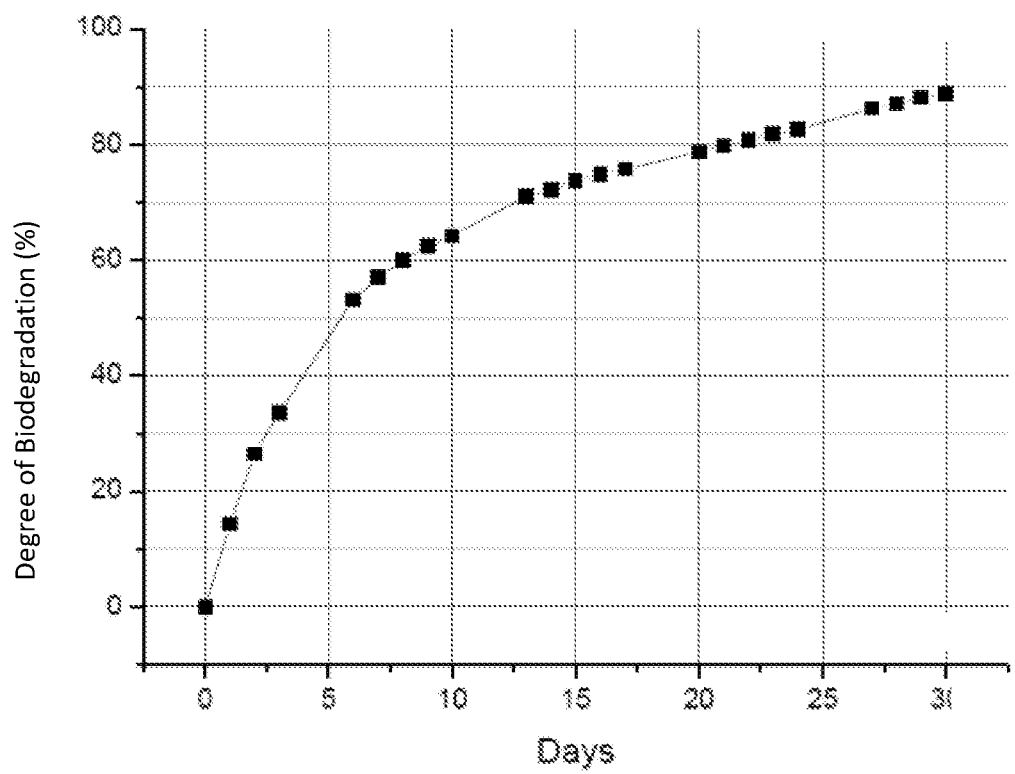
FIG. 6 shows a graph depicting biodegradation of a sample of jellyfish protein based hydrogel over time.

As evident from FIG. 6 Jelly fish protein-derived hydrogel is biodegradable and undergoes up to 90% decomposition in 30 days.

Example 7

Antibacterial Testing

Anti-bacterial activity of jellyfish protein containing Ag NP hydrogel was tested in a model using gram negative strain model bacteria Escherichia coli (E. coli). Tested bacteria were first grown in separate vessel at appropriate conditions of incubation at 37° C. for 24 hours and countable dilution of bacteria was determined by common procedure and was used to "infect" plates coated with jellyfish hydrogel. Hydrogel was prepared using Ag NP protein prepared according to example 2C. Hydrogel was formed by mixing 0.06 g of agarose with 1.2 g of jellyfish Ag NP protein (prepared in a 5:1 ratio) in 2 ml of lysogeny broth (LB) solution. The mixture was heated to 80° C. while being stirred vigorously. A volume of 0.5 ml of semi liquid hydrogel was added to each experimental plate.

Antibacterial activity of the hydrogel was determined by visual counting of bacterial colonies on each hydrogel plate after 24 hours of incubation at 37° C., and are expressed in the table below as average number of colonies per plate for three plates per sample type. Samples comprising comparable jellyfish protein-based hydrogel without silver NP and agar were used as control groups.

| Jellyfish protein hydrogel, with Ag NP | Jellyfish protein hydrogel without Ag NP | Agar with LB |
|---|---|---|
| 0 | 83 | 103 |
| 0 | 74 | 95 |
| 0 | 78 | 97 |

Visual observation of the plates showed that on reference agar plates, E. coli colonies have well defined round-shaped white colonies. No colonies of E. coli were observed on agar plates that contained jellyfish protein hydrogel, with Ag NP. Each agar plate contained in average $8.98*10^{-5}$ mole of Ag NP. Ag NP bactericidal effect resulted not only in killing the bacteria placed on the plates but also in inhibition of future bacterial growth, as no new colonies of bacteria appeared on the JFM+Ag Np plate even after 30 days of exposure of the test plates to open environment.

The bacterial growth inhibitory qualities of polymers according to embodiments of the invention may enable their incorporation in a variety of sterile medical product including: a diaper, feminine hygienic product, bandage, medical gloves, and medical wrapping material.

In the description and claims of the present application, each of the verbs, "comprise", "include" and "have" and conjugates thereof, are used to indicate that the object or objects of the verb are not necessarily a complete listing of components, elements or parts of the subject or subjects of the verb.

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims.

The invention claimed is:

1. A jellyfish polymer comprising jellyfish protein and at least one additive, wherein the additive is selected from the group consisting of: a metal particle, an antibiotic agent, a coloring, guar, agar, alginic acid or a salt thereof, agarose, cellulose, gelatin, glycerol, PVA (polyvinyl alcohol), PANPS (poly(2-acrylamido-2-methylpropanesulfonic acid)), hyaluronic acid; a nanoparticle, a carbon nanotube, a multiwalled nanotube, fullerene, a nanodot, a nanorod, a cluster compound, graphene, a metal cluster and a polyoxometalate cluster;

wherein the jellyfish protein comprises mucin and collagen.

2. The jellyfish polymer according to claim 1 wherein mucin and collagen are present in the same proportions as in naturally occurring jellyfish.

3. The jellyfish polymer according to claim 1 wherein the nanoparticle is a metal nanoparticle, semiconductor nanoparticle, metal oxide nanoparticle, ceramic nanoparticle, carbon nanoparticle or carbon nanotube.

4. The jellyfish polymer according to claim 1 wherein the nanoparticle is a silver nanoparticle.

5. The jellyfish according to claim 1 wherein the weight ratio between nanoparticle and jellyfish protein is between about 1:5 to about 5:1.

6. The jellyfish polymer according to claim 1 wherein the nanoparticles have an average diameter of about 20-60 nanometers.

7. The jellyfish polymer according to claim 6 wherein the nanoparticles have an average diameter of about 40 nanometers.

8. The jellyfish polymer according to claim 1 in the form of a hydrogel.

9. The jellyfish polymer according to claim 8, wherein upon exposure to moisture, is capable of adsorbing at least 100% of its weight in water.

10. The jellyfish polymer according to claim 9, wherein upon exposure to moisture, is capable of adsorbing at least 200% of its weight in water.

11. The jellyfish polymer according to claim 8 comprising between about 20 and about 60 percent jellyfish protein by weight.

12. The jellyfish polymer according to claim 11 comprising about 40 percent jellyfish protein by weight.

13. The jellyfish polymer according to claim 1 comprising less than 17 parts per million (PPM, by weight) Cd, less than 750 PPM Cu, less than 8.5 PPM Hg and less than 150 PPM Pb.

14. The jellyfish polymer according to claim 1 having a Young's modulus of between about 10 kilopascals and about 5000 megapascals.

15. A sanitary hygiene article comprising the polymer according to claim 1.

16. The sanitary hygiene article according to claim 15 in the form of a diaper, feminine hygienic product, bandage, medical gloves, or medical wrapping material.

17. The sanitary hygiene article according to claim 15, wherein the jellyfish protein is in the form of a hydrogel.

18. A sanitary wrapping article comprising the polymer according to claim 1.

19. The sanitary wrapping article according to claim 18 comprising a food wrapped in it.

20. A polymer according to claim 1 wherein the polymer prevents the growth of bacterial microorganisms.

21. A method of manufacturing a jellyfish-derived polymer comprising isolating jellyfish protein from jellyfish; and crosslinking the jellyfish protein to form a polymer or gelation of the protein to form a hydrogel, wherein the jellyfish protein comprises mucin and collagen.

22. The method of claim 21 wherein said mucin and collagen are not separated from each other before the polymer formation.

23. The method of claim 21, further comprising adding an additive selected from the group consisting of: a metal particle, an antibiotic agent, a coloring, guar, agar, alginic acid or a salt thereof, agarose, cellulose, gelatin, glycerol, PVA (polyvinyl alcohol), PANPS (poly(2-acrylamido-2-methylpropanesulfonic acid)), hyaluronic acid, a nanoparticle, a carbon nanotube, a multiwalled nanotube, fullerene, a nanodot, a dye, a nanorod, a cluster compound, graphene, a metal cluster and a polyoxometalate cluster.

* * * * *

UNITED STATES PATENT AND TRADEMARK OFFICE
CERTIFICATE OF CORRECTION

| | | |
|---|---|---|
| PATENT NO. | : 9,591,853 B2 | Page 1 of 1 |
| APPLICATION NO. | : 14/758965 | |
| DATED | : March 14, 2017 | |
| INVENTOR(S) | : Bogdan Belgorodsky et al. | |

It is certified that error appears in the above-identified patent and that said Letters Patent is hereby corrected as shown below:

In the Specification

Column 11, Table 3, Batch HG41b under the heading Process, "/gelatin" immediately following the word Agarose should be removed; and Column 11, Table 3, Batch HG41b under the heading Process, "glycerin" should be changed to --glycerol--; and Column 11, Table 3, Batch HG41b under the heading Process, "agar" should be changed to --agarose--; and Column 11, Table 3, Batch HG36b under the heading Process, "Agarose/gelatin" should be changed to --Gelatin--; and Column 11, Table 3, Batch HG36b under the heading Process, "glycerin" should be changed to --glycerol--; and Column 11, Table 3, Batch HG36b under the heading Process, "agar" should be changed to --gelatin--.

Signed and Sealed this
Thirteenth Day of June, 2017

Joseph Matal
*Performing the Functions and Duties of the*
*Under Secretary of Commerce for Intellectual Property and*
*Director of the United States Patent and Trademark Office*